(12) United States Patent
Chang et al.

(10) Patent No.: US 8,933,120 B2
(45) Date of Patent: Jan. 13, 2015

(54) ENHANCED BIMATOPROST OPHTHALMIC SOLUTION

(71) Applicant: Allergan, Inc., Irvine, CA (US)

(72) Inventors: Chin-Ming Chang, Tustin, CA (US); James N. Chang, Newport Beach, CA (US); Rhett M. Schiffman, Laguna Beach, CA (US); R. Scott Jordan, Trabuco Canyon, CA (US); Joan-En Chang-Lin, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/100,914

(22) Filed: Dec. 9, 2013

(65) Prior Publication Data

US 2014/0100287 A1    Apr. 10, 2014

Related U.S. Application Data

(63) Continuation of application No. 13/827,774, filed on Mar. 14, 2013, now Pat. No. 8,772,338, which is a continuation of application No. 13/715,332, filed on Dec. 14, 2012, now Pat. No. 8,586,630, which is a continuation of application No. 13/370,574, filed on Feb. 10, 2012, now Pat. No. 8,278,353, which is a continuation of application No. 12/965,514, filed on Dec. 10, 2010, now Pat. No. 8,309,605, which is a continuation of application No. 11/083,261, filed on Mar. 16, 2005, now Pat. No. 7,851,504.

(51) Int. Cl.
| | | |
|---|---|---|
| *A61K 31/19* | (2006.01) | |
| *A61K 31/215* | (2006.01) | |
| *A61K 31/5575* | (2006.01) | |
| *A61K 9/00* | (2006.01) | |
| *A61K 31/14* | (2006.01) | |
| *A61K 31/557* | (2006.01) | |
| *A61K 31/165* | (2006.01) | |

(52) U.S. Cl.
CPC ........... *A61K 31/5575* (2013.01); *A61K 9/0048* (2013.01); *A61K 31/14* (2013.01); *A61K 31/557* (2013.01); *A61K 31/165* (2013.01)
USPC .......................................... 514/530; 514/573

(58) Field of Classification Search
USPC ................................................. 514/530, 573
See application file for complete search history.

(56) References Cited

U.S. PATENT DOCUMENTS

| | | | |
|---|---|---|---|
| 4,055,602 A | 10/1977 | Nelson | |
| 4,100,192 A | 7/1978 | Morozowich | |
| 4,122,282 A | 10/1978 | Nelson | |
| 4,123,441 A | 10/1978 | Johnson | |
| 4,128,577 A | 12/1978 | Nelson | |
| 4,171,331 A | 10/1979 | Biddlecom | |
| 4,183,870 A | 1/1980 | Caton | |
| 4,303,796 A | 12/1981 | Nelson | |
| 4,382,953 A | 5/1983 | Ishii | |
| 4,543,353 A | 9/1985 | Faustini et al. | |
| 4,599,353 A | 7/1986 | Bito | |
| 4,812,457 A | 3/1989 | Narumiya et al. | |
| 4,994,274 A | 2/1991 | Chan | |
| 5,034,413 A | 7/1991 | Chan et al. | |
| 5,281,591 A | 1/1994 | Burke | |
| 5,352,708 A | 10/1994 | Woodward et al. | |
| 5,474,979 A | 12/1995 | Ding et al. | |
| 5,510,383 A | 4/1996 | Bishop et al. | |
| 5,545,665 A | 8/1996 | Burk | |
| 5,587,391 A | 12/1996 | Burk | |
| 5,607,978 A | 3/1997 | Woodward et al. | |
| 5,688,819 A | 11/1997 | Woodward | |
| 6,277,829 B1 | 8/2001 | Asero et al. | |
| 6,403,649 B1 | 6/2002 | Woodward | |
| 6,596,765 B2 | 7/2003 | Ueno | |
| 6,646,001 B2 | 11/2003 | Hellberg | |
| 6,743,439 B1 | 6/2004 | Castillo | |
| 6,933,289 B2 | 8/2005 | Lyons | |
| 7,851,504 B2 | 12/2010 | Chang | |
| 8,017,655 B2 | 9/2011 | Woodward | |
| 8,278,353 B2 | 10/2012 | Chang | |
| 8,299,118 B2 | 10/2012 | Chang | |
| 2002/0013294 A1 | 1/2002 | DeLong | |
| 2002/0103255 A1 | 8/2002 | Hellberg | |
| 2002/0177625 A1 | 11/2002 | O'Donnell | |
| 2004/0029771 A1 | 2/2004 | Rigdon | |
| 2004/0079671 A1 | 4/2004 | Bandyopadhyay et al. | |
| 2004/0115234 A1 | 6/2004 | Gewirtz | |
| 2005/0004074 A1 | 1/2005 | Lyons | |
| 2005/0276867 A1 | 12/2005 | Lyons | |
| 2006/0141049 A1 | 6/2006 | Lyons et al. | |
| 2006/0211770 A1 | 9/2006 | Chang | |

(Continued)

FOREIGN PATENT DOCUMENTS

| | | |
|---|---|---|
| CA | 2144967 | 3/1994 |
| CA | 2498233 | 3/2004 |

(Continued)

OTHER PUBLICATIONS

Alcon Laboratories, Inc., Travatan® (Travoprost Ophthalmic Solution) 0.004% Sterile, 2004, 7 Pages, NDA 21-257.

(Continued)

*Primary Examiner* — Zohreh Fay

(74) *Attorney, Agent, or Firm* — Lorenz Siddiqi

(57) ABSTRACT

A composition comprising from 0.005% to 0.02% bimatoprost by weight and from 100 ppm to 250 ppm benzalkonium chloride, wherein said composition is an aqueous liquid which is formulated for ophthalmic administration is disclosed herein.

A method which is useful in treating glaucoma or ocular hypertension related thereto is also disclosed herein.

20 Claims, 2 Drawing Sheets

(56) References Cited

U.S. PATENT DOCUMENTS

| | | | |
|---|---|---|---|
| 2009/0149546 | A1 | 6/2009 | Chang |
| 2011/0124737 | A1 | 5/2011 | Chang |
| 2012/0316243 | A1 | 12/2012 | Chang |

FOREIGN PATENT DOCUMENTS

| | | |
|---|---|---|
| DE | 2721534 | 12/1977 |
| EP | 0093380 | 11/1983 |
| EP | 0102230 | 3/1984 |
| EP | 0098141 | 11/1984 |
| EP | 0253094 | 1/1988 |
| EP | 0364417 | 4/1990 |
| EP | 0453127 | 10/1991 |
| FR | 2239458 | 7/1973 |
| FR | 2312240 | 12/1976 |
| FR | 2386523 | 11/1978 |
| FR | 2402644 | 4/1979 |
| JP | S49-069636 | 7/1974 |
| JP | S62-215537 | 9/1987 |
| JP | 2004-002358 | 1/2004 |
| LU | 68940 | 12/1973 |
| WO | 90-02553 | 3/1990 |
| WO | 92-08465 | 5/1992 |
| WO | 94-06433 | 3/1994 |
| WO | 02-07731 | 1/2002 |
| WO | 03-074038 | 9/2003 |
| WO | 2004-013119 | 2/2004 |
| WO | 2008-006235 | 1/2008 |

OTHER PUBLICATIONS

Alm, Albert et al, Uveoscleral Outflow—A Review, Experimental Eye Research, 2009, 760-768, 88(4).
Answer, Defenses and Counterclaims of Defendants Apotex Inc. and Apotex Corp., Civil Action No. 10-CV-681, *Allergan, Inc. and Duke University* v. *Apotex Inc. and Apotex Corp.*, 20 pages (Nov. 22, 2010).
Arndt, H.C., The Synthesis and Biological Activity of Prostaglandin Analogs Containing Spirocyclic Rings, Prostaglandins, 1977, 837-843, 13 (5).
Ashton, Paul et al, Formulation Influence on Conjunctival Penetration of Four Beta Blockers in the Pigmented Rabbit: A Comparison with Corneal Penetration, Pharmaceutical Research, 1991, 1166-1174, 8 (9).
Bean, Gerald, Commercially Available Prostaglandin Analogs For The Reduction of Intraocular Pressure: Similarities and Differences, Survey of Ophthalmology, 2008, S69-S84, 53 (Supp. 1).
Berglund, Barbara et al, Investigation of Structural Analogs of Prostaglandin Amides for Binding to and Activation of CB1 and CB2 Cannabinoid Receptors in Rat Brain and Human Tonsils, Adv Exp Med Biol, 1999, 527-533, 469.
Bito, L.Z. et al, The Ocular Pharmacokinetics of Eicosanoids and Their Derivatives. 1. Comparison of Ocular Eicosanoid Penetration and Distribution Following the Topical Application of $PGF_{2\alpha}$, $PGF_{2\alpha}$-1-methyl Ester, and $PGF_{2\alpha}$-1-Isopropyl Ester, Exp. Eye Res., 1987, 217-226, 44.
Bito, LZ et al, Prostaglandins, Other Eicosanoids, and Their Derivatives as Potential Antiglaucoma Agents, Glaucoma: Applied Pharmacology In Medical Treatment, 1984, 477-505, n/a.
Bito, LZ, Biological Protection with Prostanoids, CRC Press, Inc., 1985, 231-252, 1, Cohen, M. M., ed., Boca Raton, Fla.
Bito, LZ, Prostaglandins, Old Concepts And New Perspectives, Archives Of Ophthalmology, 1987, 1036-1039, 105.
Boyd, James, Quantitative Comparison of Methods of Administering Physostigmine, Archives Ophthalmology, 1943, 521-525, 30(4).
Brown, Michael, Control of Contamination in Ophthalmic Solutions, Proc. R. Sco. Med., 1967, 354-357, 60.
Brubaker, Richard et al, Effects of AGN 192024, a new Ocular Hypotensive Agent, on Aqueous Dynamics, American journal of Ophthalmology, 2001, 19-24, 131(1).
Burstein, Neal, Electrophysiologic and Morphologic Effects of Ophthalmic Preparations on Rabbit Cornea Epithelium, Invest Ophthalmol Visual Sci, 1977, 899-911, 16 (10).
Burstein, Neal, Preservative Alteration of Corneal Permeability in Humans and Rabbits, Investigative Ophthalmology & Visual Science, Dec. 1984, 1453-1457, 25(12).
Burstein, Neal, Preservative Cytotoxic Threshold For Benzalkonium Chloride and Chlorhexidine Digluconate in Cat and Rabbit Corneas, Invest. Ophthal. & Visual Sci., 1980, 308-313, 19 (3).
Cadet, Patrick et al, Molecular Identification and Functional Expression of µ3, a Novel Alternatively Spliced Variant of the Human µ Opiate Receptor Gene, J. Immunol., 2003, 5118-5123, 170.
Camber, Ola et al, Influence of Some Preservatives on the Corneal Permeability of Pilocarpine and Dexamethasone, in Vitro, International Journal of Pharmaceutics, 1987, 229-234, 39.
Camras, C.B., Reduction of Intraocular Pressure By Prostaglandins Applied topically To The Eyes Of Conscious Rabbits, Investigative Ophthalmology & Visual Science, Dec. 1977, 1125-1134, 16(12), US.
Camras, Carl B. et al, Bimatoprost, the Prodrug of a Prostaglandin Analogue, Br J Ophthalmol, 2008, 862-863, 92.
Camras, Carl B. et al, Detection of the Free Acid of Bimatoprost in Aqueous Humor Samples From Human Eyes Treated with Bimatoprost Before Cataract Surgery, The American Academy of Ophthalmology, 2004, 2193-2198, 7pg, n/a, American Academy of Ophthalmology.
Camras, Carl B. et al, Reduction of Intraocular Pressure in Normal and Glaucomatous Primate (*Aotus trivirgatus*) Eyes By Topically Applied Prostaglandin $F_{2\alpha}$, Current Eye Research, 1981, 205-209, 1 (4).
Camras, Carl et al, Intraocular Pressure Reduction with PhXA34, a New Prostaglandin Analogue, in Patients With Ocular Hypertension, Arch Ophthalmol, 1992, 1733-1738, 110.
Cantor, Louis et al, Bimatoprost: A Member of a New Class of Agents, The Prostamides, For Glaucoma Management, Exp. Opin. Invest. Drugs, 2001, 721-731, 10 (4).
Cantor, Louis et al, Levels of Bimatoprost Acid in the Aqueous Humour After Bimatoprost Treatment of Patients with Cataract, Br. J. Ophthalmol, 2007, 629-632, 91.
Cantor, Louis et al, Reply-Bimatoprost, the Prodrug of a Prostaglandin Analogue, Br J Ophthalmol, 2008, 863-864, 92.
Center for Drug Evaluation and Research, Summary Review of Application No. 22-184 (Lumigan 0.01%) (Jul. 2010).
Chang-Lin, Joan-En et al, Aqueous Humor Penetration of Topical Bimatoprost 0.01% and Bimatoprost 0.03% in Rabbits: Response to Authors, Clinical Ophthalmology, Aug. 9, 2011, 1119-1120, 5.
Cheng-Bennett, A. et al, Studies on a Novel Series of Acyl Ester Prodrugs of Prostaglandin $F_{2\alpha}$, British Journal of Ophthalmology, 1994, 560-567, 78.
Collin, Barry, Ultrastructural Changes to Corneal Stromal Cells Due to Ophthalmic Preservatives, ACTA Ophthalmologic, 1986, 72-78, 64.
Complaint For Patent Infringement: Civil Action No. 1:10-CV-681; *Allergan, Inc. and Duke University* V. *Apotex Inc. And Apotex Corp.*, 12 pages, Filed Sep. 8, 2010.
Costagliola, Ciro et al, Ocular Surface Changes Induced By Topical Application of Latanoprost and Timolol: A Short-Term Study In Glaucomatous Patients With And Without Allergic Conjunctivitis, Graefe's Arch Clin Exp Ophthalmol, 2001, 809-814, 239.
Crowston, Jonathan et al, Effect of Bimatoprost on Intraocular Pressure in prostaglandin FP Receptor Knockout Mice, Investigative Ophthalmology & Visual Science, 2005, 4571-4577, 46.
Curri, Joanne, Paragraph IV Letter to: Allergan, Inc. (Irvine, CA), Dec. 23, 2011, 12 Pages, Hi-Tech Pharmacal Co., Inc., Amityville, NY.
Davies, Sean, Hydrolysis of Bimatoprost (Lumigan) to Its Free Acid By Ocular Tissue In Vitro, Journal of Ocular Pharmacology and Therapeutics, 2003, 45-54, 19(1).
De Clercq, P., Cyclopentanones-VXL., Prostaglandin Synthesis Involving Catalytic Hydrogenation of 2,3-Dialkyl-4-Hydroxy-2-Cyclopentenones, Tetrahedron, 1976, 2747-2752, 32.
Deardorff, Dwight, Ophthalmic Preparation, Remington's Pharmaceutical Sciences, 1975, 1488, 15th ed.
Declaration of Larry Wheeler, Ph.D., 30 pages, Dec. 14, 2010.

(56) References Cited

OTHER PUBLICATIONS

Deluca, Patrick et al, Formulation of Small Volume Parenterals, Pharmaceutical Dosage Forms: Parenteral Medications, 1992, 173-248, 1.
Dubiner, Harvey, Efficacy and Safety of Bimatoprost in Patients With Elevated Intraocular Pressure: a 30-Day Comparison With Latanoprost, Surv. Ophthalmol, 2001, S353-S560, 45 (4).
Eisenberg, Dan, Bimatoprost and Travoprost: A Review of Recent Studies of Two New Glaucoma Drugs, Survey of Ophthalmology, 2002, S105-S115, 47 (1).
Faulkner, Robert, Aqueous Humor Concentrations of Bimatoprost Free Acid, Bimatoprost and Travoprost Free Acid in Cataract Surgical Patients administered Multiple Topical Ocular Doses of LUMIGAN or TRAVATAN, Journal of Ocular Pharmacology and Therapeutics, 2010, 147-156, 26(2).
FDA Label For Approved NDA 22-184 of Lumigan 0.01% and Lumigan 0.03%, Aug. 31, 2010.
Frenkel, R E et al, Evaluation of Circadian Control of Intraocular Pressure After a Single Drop of Bimatoprost 0.03% or Travoprost 0.004%, Curr. Med. Res. Opin., Apr. 2008, 919-923, 24(4).
Gandolfi, Stefano, Three-month Comparison of Bimatoprost and Latanoprost in Patients With Glaucoma and Ocular Hypertension, Adv. Ther., 2001, 110-121, 18.
Gasset, Antonio et al, Benzalkonium Chloride Toxicity to the Human Cornea, American Journal of Ophthalmology, Aug. 1977, 169-171, 84(2).
Giuffre, Giuseppe, The Effects of Prostaglandin F2α in the Human Eye, Graefe's Archive Clin. & Exper. Ophthal., 1985, 139-141, 222.
Grass, George, Mechanisms of Corneal Drug Penetration I: In Vivo and In Vitro Kinetics, Journal of Pharmaceutical Sciences, Jan. 1988, 3-14, 77 (1).
Green, Keith, Influence of Various Agents on Corneal Permeability, American Journal of Ophthalmology, 1971, 897-905, 72.
Green, Keith, Prednisolone Phosphate Penetration Into and Through the Cornea, Investigative Ophthalmology, 1974, 316-319, 13 (4).
Green, Keith, The Effects of Preservatives on Corneal Permeability of Drugs, Biopharmaceutics of Ocular Drug Delivery, 1993, 43-59.
Handbook of Pharmaceutical Excipients, Monographs for Water, Sodium Phosphate, Sodium Chloride, and Citric Acid Monohydrate (1994).
Hecht, Gerald, Chapter 89: Ophthalmic Preparations, Remington: The Science and Practice of Pharmacy, 1995, 1563-1576, 2.
Hellberg, Mark et al, The Hydrolysis of the Prostaglandin Analog Prodrug Bimatoprost to 17-Phenyltrinor PGF2α by Human and Rabbit Ocular Tissue, J. Ocular Pharmacol. Ther., 2003, 97-103, 19(2).
Higaki, Kazutaka et al, Estimation And Enhancement Of In Vitro Corneal Transport Of S-1033, A Novel Antiglaucoma Medication, International Journal Of Pharmaceutics, 1996, 165-173, 132, Elsevier, US.
Higginbotham et al., "One-Year, Randomized Study Comparing Bimatoprost And Timolol In Glaucoma And Ocular Hypertension", Archives Of Opthalmology, Oct. 2002, 1286-1293, 120 (10), US.
Ho, Norman et al, Physical Model Approach to the Design of Drugs with Improved Intestinal Absorption, Design Of Biopharmaceutical Properties Through Prodrugs & Analogs, 1977, 136-227, Edward B. Roche ed.
Honohan, Thomas, Duration of Activity of the Acid, Methyl Ester and Amide of an Orally Active Platelet Aggregation Inhibitory Prostanoid in the Rat, Prostoglandins, 1980, 139, 19.
Huang, Andrew et al, Paracellular Permeability of Corneal and Conjunctival Epithelia, Investigative Ophthalmology & Visual Science, 1989, 684-689, 30(4).
Jordan, B.A. et al, G-Protein-Coupled Receptor Heterodimerization Modulates Receptor Function, Nature, Jun. 17, 1999, 697-700, 399(6737).
Katz, Jay et al, Comparison of Human Ocular Distribution of Bimatoprost and Latanoprost, Investigative Ophthalmology & Visual Science, Jul. 2010, 1-28.

Katz, Jay, Twelve-Month, Randomized, Controlled Trial of Bimatoprost 0.01%, 0.0125%, and 0.03% in Patients with Glaucoma or Ocular Hypertension, Am J Ophthalmology, 2010, 661-671, 149(4).
Kaur, Indu Pal et al, Formulation and Evaluation of Ophthalmic Preparations of Acetazolamide, International Journal of Pharmaceutics, 2000, 119-127, 199.
Kaur, Indu Pal et al, Penetration Enhancer and Ocular Bioadhesives: Two New Avenues for Ophthalmic Drug Delivery, Drug Development and Industrial Pharmacy, 2002, 353-369, 28(4).
Keller, N. et al., Increased Corneal Permeability Induced by the Dual Effects of Transient Tear Film Acidification and Exposure to Benzalkonium Chloride, Experimental Eye Research, 1980, 203-210, 30.
Kibbe, Arthur, Benzalkonium Chloride, Handbook of Pharmaceutical Excipients, 2000, 33-35.
Laibovitz, Robert, Comparison of the Ocular Hypotensive Lipid AGN 192024 With Timolol, Arch Ophthal, 2001, 994, 119.
Lawrence, C.A., An Evaluation of Chemical Preservatives for Ophthalmic Solutions, J Am Pharm Assoc, 1955, 457, 44(8).
Lawrence, C.A., Chemical Preservatives for Ophthalmic Solutions, Am J Ophthal, 1955, 385, 39.
Lee, Vincent et al, Improved Ocular Drug Delivery with Prodrugs, Prodrugs: Topical and Ocular Drug Delivery, 1992, 221-297, Kenneth Sloan Edition.
Lee, Vincent et al, Review: Topical Ocular Drug Delivery: Recent Developments and Future Challenges, Journal of Ocular Pharmacology, 1986, 67-108, 2(1).
Liang, Y. et al, Identification and Pharmacological Characterization of the Prostaglandin FP Receptor and FP Receptor Variant Complexes, Br. J. Pharmacol., 2008, 1079-1093, 154.
Lumigan (Allergan) (Bimatoprost Ophthalmic Solution) 0.03% Product Monograph, 2001, 7 Pages.
Lumigan Package Insert, Mar. 2001, 6 pages, NDA 21-275.
Lumigan © 0,1 mg/ml, 3 pages, Jan. 2010.
Lumigan ® RC (Allergan) (Bimatoprost Ophthalmic Solution 0.01%), 2009, 7 Pages.
Lumigan, Product Description, Allergan, Inc., Jul. 2003, pp. 1-6.
Lumigan® monograph in the 57th PDR (2003).
Lyle, Donald, Early Ocular Manifestations in the Laurence-Moon-Biedl Syndrome, American Journal of Ophthalmology, 1946, 939-946, 29.
Madhu, Cherukury et al, Effect of Benzalkonium Chloride/EDTA on the Ocular Bioavailability of Ketorolac Tromethamine Following Ocular Instillation to Normal and De-epithelialized Corneas of Rabbits, Journal of Pharmaceutical Sciences, Apr. 1996, 415-418, 85(4).
Malhotra, Manjusha et al, Permeation Through Cornea, Indian Journal of Experimental Biology, Jan. 2001, 11-24, 39.
Martin, F.N., Preparation of Ophthalmic Solutions With Special Reference to Hydrogen Ion Concentration and Tonicity, Arch Ophthal, 1950, 561, 44.
Maurice, David, The Effect of the Low Blink Rate in Rabbits on Topical Drug Penetration, J Ocular Pharmacology and Therapeutics, 1995, 297-304, 11(3).
Maxey, Kirk, The Hydrolysis of Bimatoprost in Corneal Tissue Generates a Potent Prostanoid FP Receptor Agonist, Survey of Ophthalmology, Aug. 2002, S34-S40, 47 (Supp. 1).
McPherson, Samuel, Self-Sterilizing Ophthalmic Solutions, Am J Ophthal, 1949, 675, 32.
Mealy, N.E., Ophthalmic Drugs, Drugs of the Future, 2002, 509-523, 27 (5).
Medical Review, Application No. 21-275, Center for Drug Evaluation and Research, 2001.
Miller, William et al, Biological Activities of 17-Phenyl-18, 19,20-Trinorprostaglandins, Prostaglandins, Jan. 1975, 9-18, 9(1).
Mitra, Ashim, Ophthalmic Drug Delivery Systems, Drugs and the Pharmaceutical Sciences, 2003, 6 Pages, 2nd Edition (vol. 130).
Mullen, William, Ophthalmic Preservatives and Vehicles, Sury Ophthal, 1973, 469, 17(6).
Nema, Sandeep et al, Excipients—Their Role in Parenteral Dosage Forms, Encyclopedia of Pharmaceutical Technology, 2002, 1164-1187, 2.

(56) References Cited

OTHER PUBLICATIONS

Nilsson, SIV, PGF 2α Increases Uveoscleral Outflow, Invest. Ophthalmol. Vis. Sci, 1987, 284, 28 (Suppl).

Noecker, Robert et al, Corneal and Conjunctival Changes Caused by Commonly Used Glaucoma Medications, Cornea, 2004, 490-496, 23.

Noecker, Robert, Bimatoprost/Latanoprost Study Group. A Six Month Randomized Clinical Trial Comparing The Intraocular Pressure Lowering Efficacy of Bimatoprost and Latanoprost in Patients With Ocular Hypertension or Glaucoma, Am J Ophthal, 2003, 55-63, 135.

Novack, Gary et al, Commercially Available Ocular Hypotensive Products: Preservative Concentration, Stability, Storage, and In-Life Utilization, Journal of Glaucoma, 2001, 483-486, 10.

O'Brien, C.S., Carbaminoyl-choline Chloride in the Treatment of Glaucoma Simplex, Arch Ophthal, 1942, 253, 27.

O'Brien, C.S., Doryl In The Treatment of Glaucoma Simplex, Tran Am Ophthal Soc, 1941, 175, 39.

Ogundele, Abayomi et al, Impact of Topical Bimatoprost 0.01% and Bimatoprost 0.03% on Conjunctival Irritation in Rabbits, Clinical Ophthalmology, Feb. 13, 2010, 77-80, 4.

Ogundele, Abayomi et al, In Vivo Comparative Study of Ocular Vasodilation, a Relative Indicator of Hyperemia, in Guinea Pigs Following Treatment With Bimatoprost Ophthalmic Solutions 0.01% and 0.03%, Clinical Ophthalmology, Jun. 19, 2010, 649-652, 4.

Okabe, Komei et al, Effect of Benzalkonium Chloride On Transscleral Drug Delivery, Investigative Ophthalmology & Visual Science, 2005, 703-708, 46.

Parrish, Richard, A Comparison of Latanoprost, Bimatoprost, and Travoprost In Patients With Elevated Intraocular Pressure: A 12-Week, Randomized, Masked Evaluator Multicenter Study, Am J Ophthalmol, 2003, 688-703, 135.

Pfeiffer, N, New Developments in Glaucoma Drug Therapy, Ophthalmologist, 1992, W1-W13, 89.

Pfister, Roswell, The Effects of Ophthalmic Drugs, Vehicles, and Preservatives on Corneal Epithelium: a Scanning Electron Microscope Study, Effects of Opthalmic Drugs, 1976, 246-259, 15 (4).

Pharmacia & Upjohn, Xalatan (Latanoprost Ophthalmic Solution), 1998, 2 Pages.

Physicians' Desk Reference, 2004, 553-554, 58th Edition.

Physicians' Desk Reference, 56th ed., pp. 212-213, 543, 553-554, 2864-2865 (2002).

Physicians' Desk Reference, 59th ed., pp. 555-556 (2005).

Pisella, Pierre-Jean, Conjunctival Proinflammatory and Proapoptotic Effects of Latanoprost and Preserved and Unpreserved Timolol: An Ex Vivo and In Vitro Study, Investigative Ophthalmology & Visual Science, 2004, 1360-1368, 45.

Podder, SAMIR, Improving the Safety of Topically Applied Timolol in the Pigmented Rabbit Through Manipulation of Formulation Composition, Exp. Eye Res., 1992, 747-757, 54.

Poyer, J.F. et al, Prostaglandin F2α Effects on Isolated Rhesus Monkey Ciliary Muscle, Invest. Ophthalmol. Vis. Sci., Nov. 1995, 2461-2465, 36(12).

Raymond Rowe et al, Handbook of Pharmaceutical Excipients, APha Publications, 2003, 4th edition.

Remington, The Science and Practice of Pharmacy, 20th ed. at 831 (2000).

Remington, The Science and Practice of Pharmacy, 21st ed. at 864 (2005).

Remington's Pharmaceutical Sciences 1501 (15th ed. 1975).

Response from the Food and Drug Administration to Pfizer's Citizen Petition and a Supplement at 23 (Exhibit 5), 27 pages (Aug. 31, 2010).

Resul, B et al, Phenyl-substituted Prostaglandins: Potent and Selective Antiglaucoma Agents, J. Med. Chem., Jan. 22, 1993, 243-248, 36(2).

Robin, Alan et al, An Accurate Comparison of Bimatoprost's Efficacy and Adverse Effects, Arch Ophthalmol, Jul. 2002, 999-1000, 120.

Roggeband, R., Eye Irritation in Rabbit and Man After Single Applications of Equal Volumes of Undiluted Model Liquid Detergent Products, Food & Chem Toxic, 2000, 727, 38.

Romano, Maria Rosaria et al, Evidence for the Involvement of Cannabinoid DB1 Receptors in the Bimatoprost-Induced Contractions on the Human Isolated Ciliary Muscle, Investigative Ophthalmology & Visual Science, Aug. 2007, 3677-3382, 48(8).

Sandoz Paragraph IV Letter, Jul. 11, 2011, 19 Pages.

Sasaki, Hitoshi et al, Different Effects of Absorption Promoters on Corneal and Conjunctival Penetration of Ophthalmic Beta-Blockers, Pharmaceutical Research, 1995, 1146-1150, 12(8).

Sasaki, Hitoshi et al, Enhancement of Ocular Drug Penetration, Critical Reviews in Therapeutic Drug Carrier Systems, 1999, 85-146, 16(1).

Sasaki, Hitoshi et al, Ophthalmic Preservatives As Absorption Promoters For Ocular Drug Delivery, J. Pharm. Pharmacol., 1995, 703-707, 47, US.

Sasaki, Hitoshi, Modification of Ocular Permeability of Peptide Drugs by Absorption Promoters, Biol Pharm Bull, 2000, 1524, 23(12).

Sasaki, Hitoshi, Ocular Permeability of FITC-Dextran with Absorption Promoter for Ocular Delivery of Peptide Drug, J Drug Target, 1995, 129, 3.

Scholz, Martina, Pilocarpine Permeability Across Ocular Tissues and Cell Cultures: Influence of Formulation Parameters, Journal of Ocular Pharmacology and Therapeutics, 2002, 455-468, 18 (5).

Schumer, Robert et al, Medical Treatment of Glaucoma, Current Opinion in Ophthalmology, 1991, 140-150, 2.

Sharif, N.A. et al, Cat Iris Sphincter Smooth-Muscle Contraction: Comparison of FP-Class Prostaglandin Analog Agonist Activities, J. Ocul. Pharmacol. Ther, Apr. 2008, 152-163, 24(2).

Sharif, N.A. et al, Human Ciliary Muscle Cell Responses to FP-class Prostaglandin Analogs: Phosphoinositide Hydrolysis, Intracellular Ca2+ Mobilization and Map Kinase Activation, J. Ocul. Pharmacol Ther., 2003, 437-455, 19.

Sharif, N.A. et al, Human Trabecular Meshwork cell Responses Induced by Bimatoprost, Travoprost, Unoprostone, and Other FP Prostaglandin Receptor Agonist Analogues, Invest. Ophthalmol Vis. Sci., 2003, 715-721, 44.

Sharif, N.A. et al, Ocular Hypotensive FP Prostaglandin (PG) Analogs: PG Receptor Subtype Binding Affinities and Selectivities, and Agonist Potencies at FP and Other PG Receptors in Cultured Cells, Journal of Ocular Pharmacology and Therapeutics, 2003, 501-515, 19(6).

Sharif, N.A. et al, Update and Commentary on the Pro-Drug Bimatoprost and a Putative Prostamide Receptor, Expert Rev. Ophthalmol., 2009, 477-489, 4(5).

Sjoquist, Birgitta et al, Ocular and Systemic Pharmacokinetics of Latanoprost in Humans, Surv. Ophthalmol., Aug. 2002, S6-S12, 47(Suppl 1).

Sjoquist, Birgitta et al, Pharmacokinetics of Latanoprost in the Cynomolgus Monkey. 3rd Communication: Tissue Distribution After Topical Administration on the Eye Studied by Whole Body Autoradiography, Glaucoma Research Laboratories. Arzneim-Forsch/Drug Res., 1999, 240-249, 49.

Skolaut, Milton, Ophthalmic Medication, Bull Am Soc Hosp Pharm, 1948, 172, 5(4).

Spada, C.S. et al, Bimatoprost and Prostaglandin F2α Selectively Stimulate Intracellular Calcium Signaling in Different Cat iris Sphincter Cells, Exp. Eye Res., Jan. 2005, 135-145, 80(1).

Stamer, W.D. et al, Cellular Basis for Bimatoprost Effects on Human Conventional Outflow, Invest. Ophthalmol. Vis. Sci., Oct. 2010, 5176-5181, 51(10).

Starr, Michael, Further Studies on the Effects of Prostagladin on Intraocular Pressure in the Rabbit, Exp. Eye Res., 1971, 170-177, 11.

Stern, F.A., Comparison of the Hypotensive and Other Ocular Effects of Prostaglandins E2 and F2α on Cat and Rhesus Monkey Eyes, Invest Ophthal Visual Sci, 1982, 588-598, 22.

Stewart, William, Corneal Punctate Staining with Latanoprost, Bimatoprost, and Travoprost in Healthy Subjects, J Glaucoma, 2003, 475-479, 12 (6).

(56) References Cited

OTHER PUBLICATIONS

Stjernschantz, Johan et al, From PGF2α-isopropyl Ester to Latanoprost: A Review of the Development of Xalatan: The Proctor Lecture, Invest. Ophthalmol. Vis. Sci., May 2001, 1134-1145, 42(6).

Stjernschantz, Johan, Studies on Ocular Inflammation and Development of a Prostaglandin Analogue for Glaucoma Treatment, Exp. Eye Res., Apr. 2004, 759-766, 78(4).

Swan, Kenneth, Reactivity of the Ocular Tissues to Wetting Agents, American Journal of Ophthalmology, 1944, 1118-1122, 27.

Tang-Liu, Diane, Effects of Four Penetration Enhancers on Corneal Permeability of Drugs in Vitro, Journal of Pharmaceutical Sciences, 1994, 85-90, 83 (1).

Thygesen, J., Short-term Effect of Latanoprost and Timolol Eye Drops on Tear Fluid and the Ocular Surface in Patients with Primary Open-Angle Glaucoma and Ocular Hypertension, Acta Ophthal Scand, 2000, 37-41, 78.

Tonjum, Asbjorn, Permeability of Rabbit Corneal Epithelium to Horseradish Peroxidase After the Influence of Benzalkonium Chloride, Acta Ophthalmologica, Jan. 22, 1975, 335-347, 53.

TRAVATAN (travoprost ophthalmic solution) 0.004% Product Insert, NDA 21-257, Mar. 16, 2001, 7 Pages.

Van Alphen, G.W.H.M. et al, The effect of Prostaglandins on the Isolated Internal Muscles of the Mammalian Eye, Including Man, Documenta Ophthalmologica, 1977, 397-415, 42(4).

Van Der Bijl, Pieter, Effects of Three Penetration Enhancers on Transcorneal Permeation of Cyclosporine, Cornea, 2001, 505-508, 20 (5).

Vielhauer, G.A. et al, Cloning and Localization of hFP(S): a Six-Transmembrane mRNA Splice Variant of the Human FP Prostanoid Receptor, Arch Biochem Biophys., Jan. 15, 2004, 175-185, 421(2).

Walter, Modell, Pharmacologic Action of Some Ophthalmic Drugs, Arch Ophthal, 1947, 160, 37.

Walter, Thomas, 24-Hour IOP Control with Once-daily Bimatoprost, Timolol Gel-forming Solution, or Latanoprost: A 1-Month, Randomized, Comparative Clinical Trial, Survey of Ophthalmology, 2004, S26-S35, 49(1).

White, J.H. et al, Heterodimerization is Required for the Formation of a Functional GABA(B) Receptor, Nature, Dec. 17, 1998, 679-682, 396(6712).

Wilson, S.J. et al, Dimerization of the Human Receptors for Prostacyclin and Thromboxane Facilitates Thromboxane Receptor-Mediated CAMP Generation, J. Biol. Chem., Dec. 17, 2004, 53036-53047, 279(51).

Woodford, Roger, Penetration Enhancers and The Percutaneous Absorption of Drugs: An Update, J. Toxicol.—Cut & Ocular Toxicol., 1986, 167-177, 5(3).

Woodward, David et al, Bimatoprost Effects on Aqueous Humor Dynamics in Monkeys, J. Ophthalmol., 2010, 1-5, vol. 2010.

Woodward, David et al, Bimatoprost: a Novel Antiglaucoma Agent, Cardiovascular Drug Reviews, 2004, 103-120, 22(2).

Woodward, David et al, Identification of an antagonist that selectively blocks the activity of prostamides (prostaglandin-ethanolamides) in the feline iris, British Journal of Pharmacology, 2007, 342-352, 150.

Woodward, David et al, The Pharmacology of Bimatoprost (LumiganTM), Surv Ophthalmol, 2001, S337-S345, Suppl 4.

Woodward, David, Pharmacological Characterization of a Novel Antiglaucoma Agent, Bimatoprost (AGN 192024), J. Pharmacol. Exp. Ther., Jan. 24, 2003, 772-785, 305 (2).

Xalatan ® Eye Drops, Retrieval Date : Oct. 2, 2010, 3 pages, http://home.intekom.com/pharm/pharmaca/xalatan.html.

Xalatan ® product information in the PDR 59th edition, p. 2762-2763/(2005).

Xu, Ke-Ping, Corneal Organ Culture Model for Assessing Epithelial Responses to Surfactants, Tox. Sci., 2000, 306, 58.

Yamaji, K. et al, Prostaglandins E1 and E2, but not F2α or Latanoprost, Inhibit Monkey Ciliary Muscle Contraction, Curr. Eye Res., Aug. 2005, 661-665, 30(8).

ENHANCED BIMATOPROST OPHTHALMIC SOLUTION

CROSS-REFERENCE TO RELATED APPLICATION

This application is a continuation of U.S. patent application Ser. No. 13/827,774, filed Mar. 14, 2013, which is a continuation of U.S. patent application Ser. No. 13/715,332, filed Dec. 14, 2012, now U.S. Pat. No. 8,586,630, issued Nov. 19, 2013, which is a continuation of U.S. patent application Ser. No. 13/370,574, filed Feb. 10, 2012, now U.S. Pat. No. 8,278,353, issued Oct. 2, 2012, which is a continuation of U.S. patent application Ser. No. 12/965,514, filed Dec. 10, 2010, now U.S. Pat. No. 8,309,605, issued Nov. 13, 2012, which is a continuation of U.S. patent application Ser. No. 11/083,261, filed Mar. 16, 2005, now U.S. Pat. No. 7,851,504, issued Dec. 14, 2010, all of which are hereby incorporated herein by reference.

BACKGROUND OF THE INVENTION

1. Field of the Invention

This invention relates to pharmaceutical compositions comprising bimatoprost.

2. Description of Related Art

Bimatoprost, shown below, is a prostamide marketed commercially for the treatment of glaucoma and ocular hypertension.

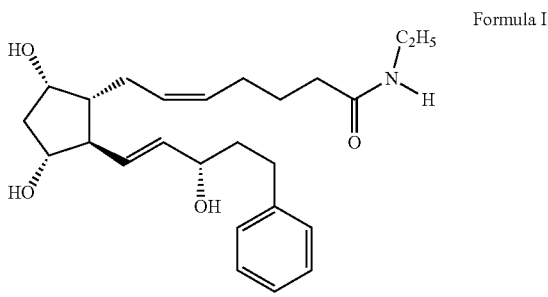 [SMILES: CCNC(=O)CCC/C=C\C[C@@H]1[C@@H](/C=C/[C@@H](O)CCc2ccccc2)[C@H](O)C[C@@H]1O]

Formula I

Benzalkonium chloride (BAK) is a preservative used in many commercial ophthalmic products to prevent microbial contamination in multi-use products. The commercial eye drops (Bimatoprost, Allergan, Inc., Irvine, Calif.) contain 0.03% bimatoprost and 0.005% BAK. Although no other prostamides are currently marketed for the treatment of glaucoma, several prostaglandin analogs are commercially available which use BAK as a preservative. These include latanoprost (Xalatan), travoprost (Travatan), and unoprostone isopropyl (Rescula), which require significantly more BAK, from 150-200 ppm, to meet antimicrobial effectiveness tests in the United States and Europe.

U.S. Pat. No. 6,596,765 B2 discloses a composition comprising 0.005% or 0.0005% latanoprost and 0.2 mg/mL BAK.

U.S. Pat. No. 6,646,001 B2 discloses compositions comprising 0.03% bimatoprost and 0.01% BAK or "0.01%+5% excess" BAK.

BRIEF DESCRIPTION OF THE DRAWING FIGURES

DETAILED DESCRIPTION OF THE INVENTION

Figure 1:
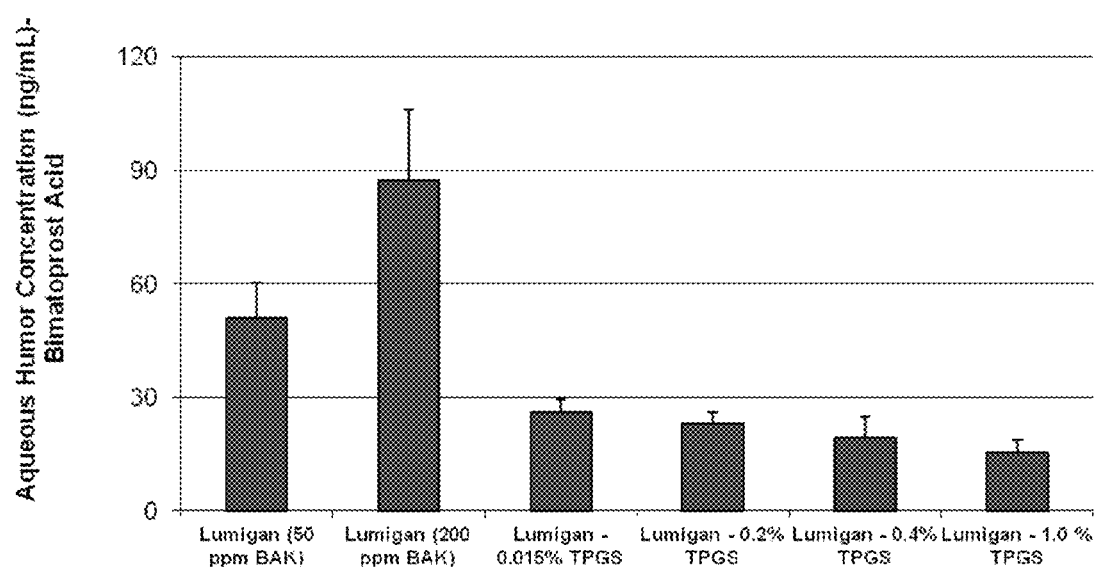
FIG. 1 is a plot showing the aqueous humor concentration of the parent acid of bimatoprost after topical administration of several formulations.

A composition comprising from 0.005% to 0.02% bimatoprost by weight and from 100 ppm to 250 ppm benzalkonium chloride, wherein said composition is an aqueous liquid which is formulated for ophthalmic administration is disclosed herein.

A method which is useful in treating glaucoma or ocular hypertension related thereto is also disclosed herein.

An aqueous liquid which is formulated for ophthalmic administration is formulated such that it can be administered topically to the eye. The comfort should be maximized as much as possible, although sometimes formulation considerations (e.g. drug stability) may necessitate less than optimal comfort.

In certain compositions the concentration of bimatoprost is from 0.01% to 0.02%. In other compositions the concentration of bimatoprost is from 0.015% to 0.02%.

In certain compositions the concentration of BAK is from 150 ppm to 200 ppm. In other compositions the concentration of BAK is from 150 ppm to 200 ppm. In other compositions the concentration of BAK is from 150 ppm to 250 ppm.

In ophthalmic compositions, a chelating agent may be used to enhance preservative effectiveness. Suitable chelating agents are those known in the art, and, while not intending to be limiting, edetate salts (EDTA) are useful chelating agents.

In certain compositions, concentration of EDTA is at least 0.001%. In other compositions, the concentration of EDTA is at least 0.01%. In other compositions the concentration of EDTA is 0.15% or less. In other compositions the concentration of EDTA is 0.1% or less. In other compositions the concentration of EDTA is 0.05% or less.

Certain compositions comprise from 150 to 250 ppm BAK and an effective amount of EDTA.

As is known in the art, buffers are commonly used to adjust the pH to a desirable range for ophthalmic use. Generally, a pH of around 6-8 is desired, and in certain compositions a pH of 7.4 is desired. Many buffers including salts of inorganic acids such as phosphate, borate, and sulfate are known.

Another commonly used excipient in ophthalmic compositions is a viscosity-enhancing, or a thickening agent. Thickening agents are used for a variety of reasons, ranging from improving the form of the formulation for convenient administration to improving the contact with the eye to improve bioavailability. The viscosity-enhancing agent may comprise a polymer containing hydrophilic groups such as monosaccharides, polysaccharides, ethylene oxide groups, hydroxyl groups, carboxylic acids or other charged functional groups. While not intending to limit the scope of the invention, some examples of useful viscosity-enhancing agents are sodium carboxymethylcellulose, hydroxypropylmethylcellulose, povidone, polyvinyl alcohol, and polyethylene glycol.

In ophthalmic solutions, tonicity agents often are used to adjust the composition of the formulation to the desired isotonic range. Tonicity agents are well known in the art and some examples include glycerin, mannitol, sorbitol, sodium chloride, and other electrolytes.

One composition has a pH of 7.4 and consists essentially of 0.015% bimatoprost, 200 ppm benzalkonium chloride, from 0 to 0.03% EDTA, a phosphate buffer, NaCl, and water.

Another composition has a pH of 7.4 and comprises 0.02% bimatoprost, 200 ppm benzalkonium chloride, from 0 to 0.03% EDTA, a phosphate buffer, NaCl, and water.

Another composition has a pH of 7.4 and consists of 0.01% bimatoprost, 200 ppm benzalkonium chloride, from 0 to 0.03% EDTA, a phosphate buffer, NaCl, and water.

The best mode of making and using the present invention are described in the following examples. These examples are given only to provide direction and guidance in how to make and use the invention, and are not intended to limit the scope of the invention in any way.

One embodiment comprises 0.01% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment comprises 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment comprises 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment comprises 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists essentially of 0.01% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists essentially of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists essentially of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment consists essentially of 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.01% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment consists of 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Example 1

Formulations containing 0.268% sodium phosphate dibasic heptahydrate, 0.014% citric acid, 0.83% sodium chloride, with the pH adjusted to 7.3 in qs water, and the amounts of bimatoprost, BAK, and EDTA listed in Table 1 below were prepared by conventional methods well known in the art.

TABLE 1

| Formulation |
| --- |
| 1. 0.03% Bimatoprost (50 ppm BAK) Control |
| 2. 0.03% Bimatoprost - 200 ppm BAK |
| 3. 0.03% Bimatoprost - 0.015% TPGS (no preservative) |
| 4. 0.03% Bimatoprost - 0.2% TPGS (no preservative) |
| 5. 0.03% Bimatoprost - 0.4% TPGS (no preservative) |
| 6. 0.03% Bimatoprost - 1.0% TPGS (no preservative) |

Example 2

Studies were carried out to determine the effect of benzalkonium chloride (BAK) and d-alpha tocopheryl polyethylene glycol 1000 succinate (TPGS) on ocular absorption of bimatoprost in vivo. For the in vivo study, eighteen female rabbits were given a single 28 μL eyedrop bilaterally and aqueous humor samples were collected (n=3 animals with 6 eyes per formulation) at 60 min postdose. Two rabbits (4 eyes) remained untreated to serve as pre-dose bioanalytical controls. Bimatoprost and its parent carboxylic acid extracted from aqueous humor and in vitro samples were analyzed by a liquid chromatography tandem mass spectrometry (LC-MS/MS) method with a quantitation range of 0.25-60 ng/mL.

Due to extensive metabolism of bimatoprost in rabbit eyes, its parent acid was used as a surrogate for determining ocular absorption of bimatoprost. Concentration of the acid in rabbit aqueous humor following single dose of 6 different bimatoprost formulations are summarized in FIG. 1 and Table 2 below.

TABLE 2

| Formulation | Aqueous Humor$^a$ (ng/mL) |
| --- | --- |
| 1. 0.03% Bimatoprost (50 ppm BAK) Control | 51.0 ± 9.4 |
| 2. 0.03% Bimatoprost - 200 ppm BAK | 87.2 ± 19.0* |
| 3. 0.03% Bimatoprost - 0.015% TPGS (no preservative) | 26.1 ± 3.3* |
| 4. 0.03% Bimatoprost - 0.2% TPGS (no preservative) | 22.9 ± 3.2* |
| 5. 0.03% Bimatoprost - 0.4% TPGS (no preservative) | 19.3 ± 5.6* |
| 6. 0.03% Bimatoprost - 1.0% TPGS (no preservative) | 15.4 ± 3.3* |

$^a$Mean ± SD. Per formulation, N = 3 rabbits (6 eyes).
*Statistically different (p < 0.05) compared to 0.03% Bimatoprost Test formulations containing 0.015%, 0.2%, 0.4% and 1.0% TPGS resulted in a lower aqueous humor carboxylic acid concentration compared to Bimatoprost by 52%, 59%, 62% and 72%, respectively. In contrast, 0.03% Bimatoprost containing 200 ppm BAK resulted in 57% higher aqueous humor AGN 191522 concentration compared to Bimatoprost (50 ppm BAK).

While not intending to limit the scope of the invention in any way, or be bound by theory, compared to the Bimatoprost control, formulations containing TPGS resulted in decrease bimatoprost permeability. In contrast, formulations with higher BAK resulted in higher permeability.

Example 3

Formulations containing 0.268% sodium phosphate dibasic heptahydrate, 0.014% citric acid, 0.83% sodium chloride, with the pH adjusted to 7.3 in qs water, and the amounts of bimatoprost, BAK, and EDTA listed in Table 3 below were prepared by conventional methods well known in the art.

TABLE 3

Formulation

A. 0.03% Bimatoprost (50 ppm BAK) - Control
B. 0.015% Bimatoprost (50 ppm BAK)
C. 0.015% Bimatoprost (50 ppm BAK) 0.03% EDTA
D. 0.015% Bimatoprost (200 ppm BAK)
E. 0.015% Bimatoprost (200 ppm BAK) 0.03% EDTA
F. 0.015% Bimatoprost (50 ppm BAK) 0.015% EDTA
G. 0.015% Bimatoprost (200 ppm BAK) 0.015% EDTA
H. 0.015% Bimatoprost (125 ppm BAK)
I. 0.015% Bimatoprost (125 ppm BAK) 0.03% EDTA
J. 0.015% Bimatoprost (125 ppm BAK) 0.015% EDTA
K. 0.015% Bimatoprost (150 ppm BAK)
L. 0.015% Bimatoprost (150 ppm BAK) 0.1% EDTA
M. 0.015% Bimatoprost
N. 0.03% Bimatoprost Example 4

The effect of benzalkonium chloride (BAK) and ethylenediaminetetraacetic acid (EDTA) on bimatoprost permeability across primary culture of rabbit corneal epithelial cell layers (RCECL). Corneal epithelial cells were harvested from New Zealand White rabbits and cultured on Transwell™ filters until confluency (Day 5). For the transport experiment, cells were first equilibrated in transport buffer for 1 hour at 37° C. Dosing solution containing 0.015% or 0.03% bimatoprost with varying concentrations of BAK and EDTA was then applied to the apical compartment of the Transwell™ (2 cultures; n=3-4 per culture) and the cells were incubated at 37° C. At 30, 60, 90 and 120 minutes postdose, 200 μL samples were taken from the basolateral chamber for apical to basolateral (AB) transport. The samples were analyzed by a liquid chromatography tandem mass spectrometry (LC-MS/MS) method with quantitation range of 1-600 ng/mL.

Figure 2:
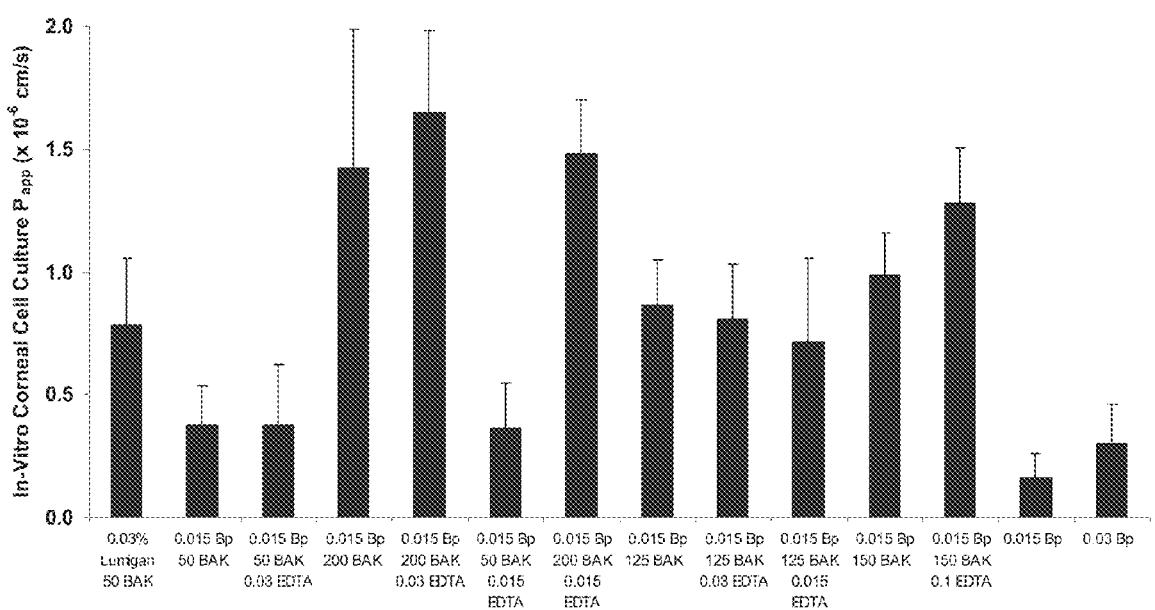
FIG. 2 is a plot showing the membrane permeability of bimatoprost in several different formulations.

The results are presented in FIG. 2.

Example 5

A drop of formulation J is administered once daily topically to the eye of a person suffering from glaucoma. After a few hours, intraocular pressure drops more and less hyperemia is observed than would be observed for formulation A. Lowered intraocular pressure persists for as long as the treatment continues.

What is claimed is:

1. An ophthalmic composition comprising about 0.01%-0.015% w/v bimatoprost and about 0.02% w/v benzalkonium chloride.

2. The ophthalmic composition of claim 1, wherein the composition comprises about 0.01% w/v bimatoprost.

3. The ophthalmic composition of claim 1, wherein the composition comprises 0.01% w/v bimatoprost.

4. The ophthalmic composition of claim 1, wherein the composition comprises about 0.015% w/v bimatoprost.

5. The ophthalmic composition of claim 1, wherein the composition comprises 0.015% w/v bimatoprost.

6. The ophthalmic composition of claim 1, wherein the composition comprises 0.02% w/v benzalkonium chloride.

7. The ophthalmic composition of claim 1, wherein the composition further comprises dibasic sodium phosphate.

8. The composition of claim 1, wherein the first composition further comprises citric acid monohydrate.

9. The composition of claim 1, wherein the composition further comprises sodium chloride.

10. The composition of claim 1, wherein the first composition further comprises hydrochloric acid and sodium hydroxide to adjust the pH.

11. The composition of claim 1, wherein the composition further comprises water.

12. The composition of claim 1, wherein the first composition has a pH of about 7.3.

13. The composition of claim 1, wherein the composition comprises 0.01% w/v bimatoprost and 0.02% w/v benzalkonium chloride, and when applied to the eyes of a human patient suffering from elevated intraocular pressure, lowers intraocular pressure and results in less hyperemia than a second composition comprising 0.03% w/v bimatoprost and 0.005% w/v benzalkonium chloride.

14. The composition of claim 13, wherein the composition applied once daily lowers intraocular pressure as effectively as the second composition applied once daily.

15. The composition of claim 13, wherein the composition is applied to the eyes of a human patient suffering from elevated intraocular pressure at least once a day.

16. The composition of claim 13, wherein the composition applied once daily lowers intraocular pressure more effectively than the second composition applied once daily.

17. The composition method of claim 13, wherein the composition applied once daily is effective for treating glaucoma.

18. The composition of claim 1, wherein the composition comprises 0.01% w/v bimatoprost and 0.02% w/v benzalkonium chloride, and when applied once daily to the eyes of a human patient suffering from elevated intraocular pressure, lowers intraocular pressure and results in less hyperemia than a second composition comprising 0.03% w/v bimatoprost and 0.005% w/v benzalkonium chloride.

19. The composition of claim 18, wherein the composition applied once daily lowers intraocular pressure as effectively as the second composition applied once daily.

20. The composition method of claim 18, wherein the composition applied once daily is effective for treating glaucoma.

* * * * *

UNITED STATES PATENT AND TRADEMARK OFFICE
CERTIFICATE OF CORRECTION

PATENT NO. : 8,933,120 B2
APPLICATION NO. : 14/100914
DATED : January 13, 2015
INVENTOR(S) : Chin-Ming Chang et al.

It is certified that error appears in the above-identified patent and that said Letters Patent is hereby corrected as shown below:

On the Title Page

On the page 2, in column 1, under "Other Publications", line 35, delete "Sco." and insert -- Soc. --, therefor.

On the page 3, in column 1, under "Other Publications", line 51, delete "Opthalmology," and insert -- Ophthalmology, --, therefor.

On the page 3, in column 1, under "Other Publications", line 58, delete "Prostoglandins," and insert -- Prostaglandins, --, therefor.

On the page 3, in column 1, under "Other Publications", line 67, delete "Jul. 2010," and insert -- Jul. 9, 2010, --, therefor.

On the page 3, in column 2, under "Other Publications", line 35, delete "Lumigan ©" and insert -- Lumigan ® --, therefor.

On the page 3, in column 2, under "Other Publications", line 68, delete "Sury" and insert -- Surv --, therefor.

On the page 4, in column 1, under "Other Publications", line 36, delete "Opthalmic" and insert -- Ophthalmic --, therefor.

On the page 4, in column 2, under "Other Publications", line 64, delete "Prostagladin" and insert -- Prostaglandin --, therefor.

In the Claims

In column 6, line 38, in claim 17, after "composition" delete "method".
In column 6, line 51, in claim 20, after "composition" delete "method".

Signed and Sealed this
Twenty-eighth Day of April, 2015

Michelle K. Lee
*Director of the United States Patent and Trademark Office*